United States Patent [19]

Pettit et al.

[11] Patent Number: 5,436,400
[45] Date of Patent: Jul. 25, 1995

[54] ISOLATION AND STRUCTURE OF SPONGISTATIN 1

[75] Inventors: George R. Pettit, Paradise Valley; Zbigniew A. Cichacz; Cherry L. Herald, both of Tempe, Ariz.

[73] Assignee: Arizona Board of Regents, Tempe, Ariz.

[21] Appl. No.: 6,270

[22] Filed: Jan. 19, 1993

[51] Int. Cl.$^6$ ............................................. C07D 323/00
[52] U.S. Cl. ....................................................... 549/267
[58] Field of Search ........................ 514/450; 549/267

[56] References Cited

U.S. PATENT DOCUMENTS 5,196,447  3/1993  Pettit et al. ........................ 549/267

*Primary Examiner*—C. Warren Ivy
*Assistant Examiner*—A. A. Owens
*Attorney, Agent, or Firm*—Richard R. Mybeck

[57] ABSTRACT

An Eastern Indian Ocean marine sponge in the genus Spongia was located in the Republic of the Maldives and found to contain a structurally unprecedented macrocyclic lactone named spongistatin 1. The new perhydropyran-containing structure, as shown below, was found to be remarkably potent and specific, log molar $TCI_{50}$ to $< -10$, against twenty human cancer cell lines in the U.S. National Cancer Institute's panel of sixty.

2 Claims, No Drawings

ISOLATION AND STRUCTURE OF SPONGISTATIN 1

INTRODUCTION

The present invention relates to the discovery and isolation of new and extremely potent constituent of an Eastern Indian Ocean marine sponge of the genes Spongia herein denominated "spongistatin 1". This new perhydropan-containing structure was found to be remarkably potent and specific against twenty human cancer cell lines in the U.S. National Cancer Institute's panel. Some of the work described herein was supported by NCI Grant CA-16049-07-12. The United States government may have certain rights to this invention.

BACKGROUND OF THE INVENTION

A great number of ancient marine invertebrate species in the Phyla Bryozoa, Mollusca and Porifera were well established in the earth's oceans over one billion years ago. Certainly such organisms had explored trillions of biosynthetic reactions in their evolutionary chemistry to reach present levels of cellular organization, regulation and defense. Marine sponges have changed minimally in physical appearance for nearly 500 million years, suggesting a very effective chemical evolution in response to changing environmental conditions for at least that time period. Some recognition of the potential for utilizing biologically potent marine animal constituents was recorded in Egypt about 2,700 BC, and by 200 BC sea hare extracts were being used in Greece for medicinal purposes. Such considerations, combined with the general observation that marine organisms (especially invertebrates and sharks) rarely develop cancer, led to the first systematic investigation of marine animal and plant anticancer constituents.

By 1968 ample evidence had been obtained, based on the U.S. National Cancer Institute's key experimental cancer systems, that certain marine organisms would provide new and structurally novel antineoplastic and/or cytotoxic agents. Analogous considerations suggested that marine organisms could also provide effective new drugs for other severe medical challenges, such as viral diseases. Furthermore, marine organisms were expected to contain potentially useful drug candidates (and biochemical probes) of unprecedented structural types, that would have eluded discovery by contemporary techniques of medicinal chemistry. Fortunately, some of these expectations have been realized in the intervening period. Illustrative of these successes are the discoveries of the bryostatins, dolastatins, and cephalostatins by the Cancer Research Institute in Tempe, Ariz. where several members of these series of remarkable anticancer drug candidates are either now in human clinical trial or preclinical development. See U.S. Pat. Nos. 4,816,444, 4,833,257, 4,873,245, and 4,879,278.

As is well known to those presently engaged in medical research, the time between the isolation of a new compound, and its introduction to the market place takes at least several years in the best case and can take several decades. Consequently, industry, in association with the government, has devised a number of qualifying tests which serve two purposes. One purpose is to eliminate those substances whose results in the qualifiers unequivocally demonstrate that the further expenditure of funds on developing those substances would be economically counter-productive. The second, and more important purpose, is to identify those substances which demonstrate a high likelihood of success and therefore warrant the requisite further investment necessary to obtain the data which is required to meet the various regulatory requirements imposed by those governments which regulate the market place into which such substances will enter.

The present cost of obtaining such data approaches Ten Million Dollars ($10,000,000 U.S.) per substance. Economics dictate that such an investment not be made unless there is a reasonable likelihood that it can be recovered. Absent such an opportunity, there will be no such investment, and without investment, the research requisite for the discovery of potentially life saving drugs will stop.

Only two hundred years ago, many diseases ravaged humankind. Many of these diseases now have been controlled or eradicated. In the development of the means to treat or control these diseases, work with the appropriate common experimental animals was of critical importance. With the various types of cancers, and with the HIV virus, such work is presently ongoing. The research for the treatment of various types of cancer is coordinated in the United States by the National Cancer Institute (NCI). NCI, as a government entity, has been charged with assisting anti-cancer research. To establish whether a substance has anti cancer activity, NCI has established a variety of protocols, one of which involves testing the candidate substance against a cell line panel containing 60 human tumor cell lines. This protocol has been verified and is generally accepted throughout the scientific community. This protocol and the established statistical means of evaluating the results obtained therefrom have been fully described in the literature. See *Principles & Practice of Oncology* PPO Updates, Volume 3, Number 10, October 1989, by Michael R. Boyd, M.D., Ph.D., for an indepth description of the test protocol. The statistical analysis is explained in "Display and Analysis of Patterns of Differential Activity of Drugs Against Human Tumor Cell Lines: Development of Means Graph and COMPARE Algorithm" *Journal of the National Cancer Institute* Reports Vol. 81, No. 14, Pg. 1088, Jul. 14, 1989, by K. D. Paull et al. Both of these references are incorporated herein by this reference thereto.

The Constitution of the United States (Art. 1, Sec. 8) authorizes Congress to establish the United States Patent and Trademark Office (USPTO) to promote scientific advancement. This obligation can only be fully met when the USPTO accepts current medical and scientific realities in the area of medical research.

The Framers of the Constitution meant to advance scientific advancement. Cells are alive. The impairment of human tumor cell growth is utility. The sole right obtained from the grant of Letters Patent is the right to prevent others from exploiting the subject matter of the patent. The recognition of cell line data as a measure of antineoplastic activity and therefor an acceptable showing of "utility" can aid research in the United States, and thereby save the citizens of the United States from being held hostage by foreign governments or foreign corporations, if such research is no longer viable in the United States.

Numerous compounds have been discovered which demonstrate significant antineoplastic activity. As discussed above, many of these compounds have been extracted, albeit with great difficulty, from living creatures such as the sponge or the sea hare. However, once the isolation and testing of such compounds has progressed, a practical problem exists, namely, how to obtain a significant quantity of the compound.

Unlike cinchona bark which is collected to produce quinine and has an excellent yield, the collection and processing of the compounds of the present invention in the natural occurring state ranges from the grossly impractical to the utterly impossible. Even ignoring potential ecological effects, the population of such creatures is clearly insufficient. Accordingly, the elucidation of the absolute structure of such antineoplastic compounds is essential.

A major component of vigorous efforts for over two decades has been directed at marine sponge antineoplastic and/or cytotoxic biosynthetic products and it is toward the furtherance of that effort that the present invention is directed.

BRIEF SUMMARY OF THE INVENTION

Marine Porifera in the genus Spongia (family Spongiidae, Class Demospongiae) have proved to be good sources of tetracyclic diterpenes. Based on previous investigations the Spongia would not seem a particularly attractive reservoir of antineoplastic macrocyclic lactones. But natural products are replete with surprises. We are very pleased to report discovery in a Spongia sp. a macrocyclic lactone designated spongistatin 1 that possesses a remarkable structure exhibiting phenomenally potent (and selective) activity against twenty of the U.S. national Cancer Institute's (NCI) panel of sixty human cancer cell lines.

A 1988 recollection (400 kg wet wt.) of the dark brown (to black) Spongia sp. from the Eastern Indian Ocean (Republic of the Maldives), was extracted with methanol followed by methylene chloride-methanol. A methylene chloride fraction derived from the combined extract was carefully separated (guided by P388 lymphocytic leukemia bioassay) employing an extensive series of LH-20 SEPHADEX gel permeation and partition (also on SILICA GEL) chromatographic procedures followed by final isolation using reversed phase (PREPEX 5-20μ, C8 column) high performance liquid chromatography with 5:5:7 acetonitrile-methanol-water as eluent to afford (13.8 mg, 5.1 $10^{-4}$ yield) colorless spongistatin 1 as an amorphous powder, mp 161°–162° C.; $[\alpha]^{22}D+26.2°$ (c=0.32, $CH_3OH$); UV ($CH_3OH$) $\lambda_{max}$ 216 nm, ε 8490; IR (film) 3430, 2928, 1736, 1383, 1232, 1177, 1085, 993 $cm^{-1}$ and high resolution FAB MS, m/z 1245.5949 (M+Na)+ corresponding to $C_{63}H_{95}ClO_{21}Na$ (calcd. mass 1245.5952) with low resolution FAB peaks at m/z 1245.5 [M+Na]+ as parent peak and 1187.5 [M-35] representing loss of chlorine.

Spongistatin 1 has the following structure:

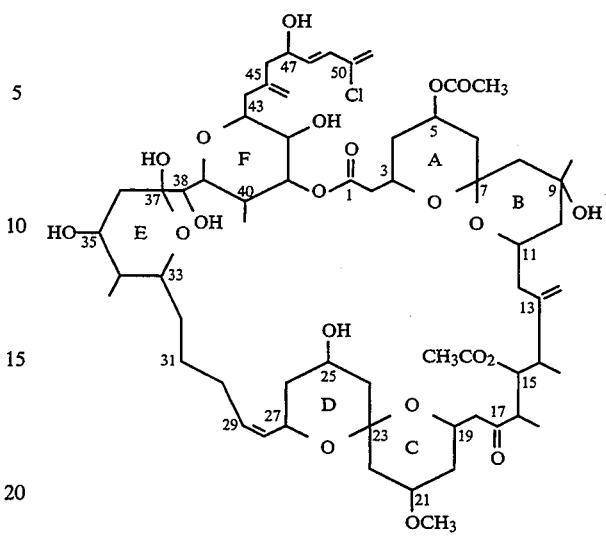

Accordingly, the principal object of the present invention is the isolation of a structurally unprecedented macrocyclic lactone herein denominated "spongistatin 1" having a log molar $TGI_{50}$ of about $<-10$ against various human cancer cell lines.

Another object of the present invention is the structural elucidation of the substance denominated "spongistatin 1".

These and still further objects as shall hereinafter appear are readily fulfilled by the present invention in a remarkably unexpected manner as will be readily discerned from the following detailed description of an exemplary embodiment thereof.

DESCRIPTION OF PREFERRED EMBODIMENTS

Structural elucidation of spongistatin 1 was especially challenging and required three separate (and in-depth), high field 400 and 500 MHz 2 D NMR analyses (APT, $^1H$-$^1H$-COSY, $^1H$-$^{13}C$-COSY, HMBC, and NOE) employing acetonitrile-$d_3$, pyridine-$d_5$ and methanol-$d_3$ solvent systems. The assignments are recorded in Table 1. Results of a series of selective acetylation experiments assisted in deducing some of these assignments.

Spongistatin 1 was found to be incredibly active and selective against twenty (CCRF-CEM, HL-60, SR leukemias; NCI-H226, NCI H23, NCI H460, NCI H522 non-small cell lung; DMS 114, and 273 small cell lung; Colo 205, DCC-2998, HCT-116, RT29, KM 2022 colon; SF-239. U-251 CNS; SK-MEL-5 melanoma; OVCAR-3 and -8 ovarian; and A-498 renal cancers) of the NCI panel of sixty human cancer cell lines with log molar $TGI_{50}$ ranging from −8.98 to $<-10.00$. Table I. NMR assignments for spongistatin 1 recorded in $CD_3CN$. Coupling constants are in Hz (in parenthesis). The mixing time for the HMBC was set at 130 microsecond).

| $^{13}C$ (100 MHz) | | XHCorr. (400 MHz) | HMBC(500 MHz, C to H) |
|---|---|---|---|
| *1 | 173.07 | | H-2;H-41 |
| 2 | 40.86 | 2.44 dd(10,18) 2.53 dd(2,18) | H-4 |
| 3 | 63.59 | 4.25 brt(10) | H-2;H-8 |
| 4 | 34.65 | 1.55*;1.68* | H-2;H-6 |
| 5 | 67.06 | 4.92 brs | |
| 6 | 38.17 | 1.67 dd(5,14); | H-5;H-8 |

| 13C (100 MHz) | XHCorr. (400 MHz) | HMBC(500 MHz, C to H) |
|---|---|---|
| | 1.78 brd(14) | |
| 7 | 99.26 | H-6;H-8;H-9a |
| 8 | 46.76 | 1.47 d(14);1.60* | H-9a;H-6 |
| 9 | 69.64 | | H-9a;OH(C9);H-8 |
| 9a | 30.21 | 1.06 s | H-8;H-10 |
| 10 | 44.96 | 1.28*;1.55* | H-9a;H-12;H-8 |
| 11 | 65.00 | 4.25 brt(10) | H-12;H-13a;H-15;H-6 |
| 12 | 44.24 | 1.99*;2.27 brd(14) | H-10;H-13a |
| 13 | 148.03 | | H-12;H-13a;H-14a;H-15 |
| 13a | 114.86 | 4.83 brs;4.83 brs | H-12;H-14 |
| 14 | 36.60 | 2.78* | H-13a;H-14a;H-15; H-16;H-12 |
| 14a | 12.09 | 1.04 d(6.9) | H-15 |
| 15 | 75.34 | 5.12 dd(1.7,11) | H-13a;H-14a;H-16;H-16a |
| 16 | 47.62 | 3.04 dq(7,11) | H-15;H-16a |
| 16a | 13.73 | 1.15 d(7) | H-15;H-16 |
| 17 | 213.52 | | H-16;H-16a;H-18;H-15 |
| 18 | 51.94 | 2.62 brd(18) 2.86 dd(11,18) | H-16;H-20 |
| 19 | 66.16 | 4.00 brt(11) | H-18 |
| 20 | 37.70 | 0.97 ddd(12,12,12); 1.98* | H-18;H-22 |
| 21 | 73.98 | 3.46 tt(4,4,12,12) | H-22;H—OMe;H-20 |
| 22 | 44.18 | 1.08 t(12);1.99* | H-21;H-20 |
| 23 | 99.91 | | H-18;H-22;H-24;H-27 |
| 24 | 34.91 | 1.55*;2.28* | H-22 |
| 25 | 64.41 | 3.93 brm | H-26;H-27;H-24 |
| 26 | 39.11 | 1.57*;1.57* | H-28;H-24 |
| 27 | 61.22 | 5.00 ddd(4.3,10,10) | H-26;H-29 |
| 28 | 131.22 | 5.32 brt(10) | H-27;H-30 |
| 29 | 133.42 | 5.48 ddd(10,10,10) | H-27;H-30 |
| 30 | 28.07 | 2.00*;2.19* | H-28;H-29;H-31;H-32 |
| 31 | 27.04 | 1.23*;1.60* | H-29;H-33;H-30;H-32 |
| 32 | 32.82 | 1.30 m;1.42 m | H-33 |
| 33 | 67.15 | 4.13 dt(3.4,3.4,8) | H-34a |
| 34 | 39.32 | 1.57 m | H-34a;H-36 |
| 34a | 11.55 | 0.81 d(7) | H-33;H-34 |
| 35 | 71.47 | 3.65 brs | H-34a;H-33;H-36 |
| 36 | 33.79 | 1.61*;1.89* | OH(C37);H-34 |
| 37 | 99.41 | | H-33;H-36;OH(C37),H-38 |
| 38 | 73.11 | 3.34 brs | H-36 |
| 39 | 81.30 | 3.72 brd(10) | H-40a;H-41 |
| 40 | 37.26 | 1.91* | H-40a;H-39;H-41 |
| 40a | 12.69 | 0.74 d(7) | H-40;H-41 |
| 41 | 80.60 | 4.75 dd(9,11) | H-40a;H-39;H-40; H-42;H-43 |
| 42 | 73.11 | 3.12 t(9) | H-40;H-41;H-43;H-40a |
| 43 | 78.72 | 3.39 brt(9) | H-39;H-41;H-42;H-44 |
| 44 | 40.24 | 2.08*;2.76 brd(13) | H-42;H-46;H-45a |
| 45 | 144.00 | | H-45a;H-43;H-44; H-46;H-47 |
| 45a | 116.61 | 4.86 brs;4.89 brs | H-44;H-46 |
| 46 | 43.93 | 2.33 brdd(7,14); 2.19* | H-44;H-45a |
| 47 | 70.13 | 4.36 ddd(6,7,11) | H-46;H-48 |
| 48 | 139.21 | 6.11 dd(6,15) | H-46;H-47 |
| 49 | 126.99 | 6.41 brd(15) | H-47;H-48;H-51 |
| 50 | 139.21 | | H-48;H-49;H-51 |
| 51 | 116.48 | 5.35 brs;5.45 brs | H-48;H-49 |
| OMe | 55.72 | 3.24 s | H-21 |
| OAc | 21.78 171.61 | 1.94 s | H—OAc(δ1.94);H-5 |
| OAc | 21.00 170.21 | 1.84 s | H—OAc(δ1.84);H-15 |
| OH (C25) | | 4.39 d(9.9) | |
| OH (C37) | | 4.73 d(2) | |
| OH (C9) | | 4.32 brs | |
| OH | | 3.83 brm | |

*Coupling constants for these signals were not measured due to overlapping.

The derived physical structure of the compound named herein as spongistatin 1 is as follows.

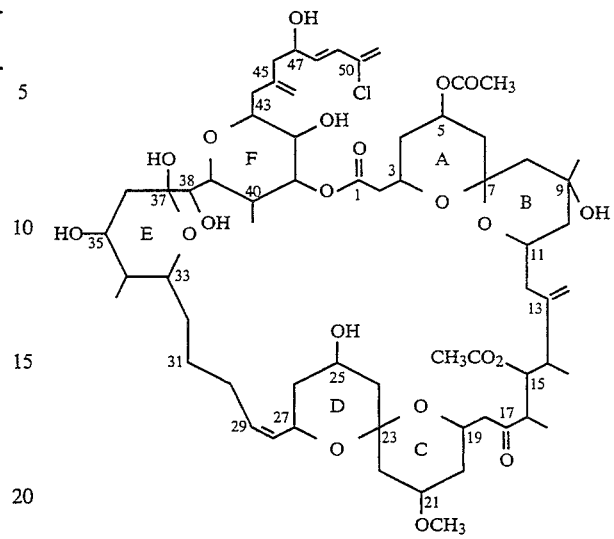

From the foregoing it is apparent that an invention has been herein described and illustrated which fulfills all of the aforestated objectives in a remarkably unexpected fashion. It is of course understood that such modifications, alterations and adaptations as may readily occur to the artisan confronted with this disclosure are intended within the spirit of this disclosure which is limited only by the scope of the claims appended herein.

Accordingly, what is claimed is:

1. A substantially pure composition of matter denominated spongistatin 1 having the following structural formula:

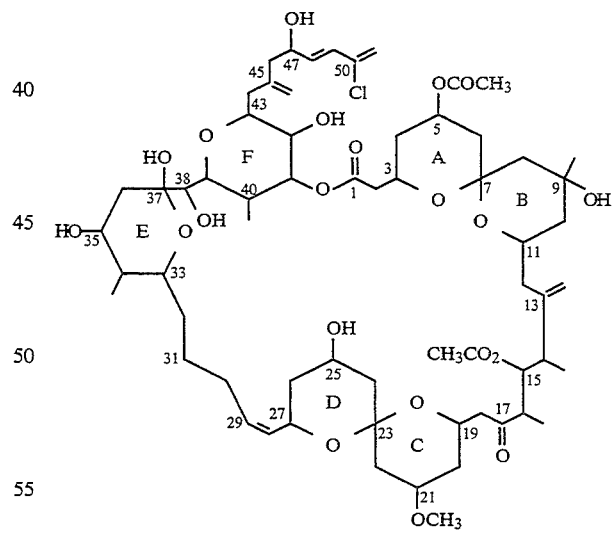

2. A composition of matter according to claim 1 having, when recorded in $CD_3CD$, the NMR assignments;

| 13C (100 MHz) | XHCorr. (400 MHz) | HMBC(500 MHz, C to H) |
|---|---|---|
| 1 | 173.07 | | H-2;H-41 |
| 2 | 40.86 | 2.44 dd(10,18) 2.53 dd(2,18) | H-4 |
| 3 | 63.59 | 4.25 brt(10) | H-2;H-8 |
| 4 | 34.65 | 1.55*;1.68* | H-2;H-6 |

-continued

| $^{13}C$ (100 MHz) | | XHCorr. (400 MHz) | HMBC(500 MHz, C to H) |
|---|---|---|---|
| 5 | 67.06 | 4.92 brs | |
| 6 | 38.17 | 1.67 dd(5,14); 1.78 brd(14) | H-5;H-8 |
| 7 | 99.26 | | H-6;H-8;H-9a |
| 8 | 46.76 | 1.47 d(14);1.60* | H-9a;H-6 |
| 9 | 69.64 | | H-9a;OH(C9);H-8 |
| 9a | 30.21 | 1.06 s | H-8;H-10 |
| 10 | 44.96 | 1.28*;1.55* | H-9a;H-12;H-8 |
| 11 | 65.00 | 4.25 brt(10) | H-12;H-13a;H-15;H-6 |
| 12 | 44.24 | 1.99*;2.27 brd(14) | H-10;H-13a |
| 13 | 148.03 | | H-12;H-13a;H-14a;H-15 |
| 13a | 114.86 | 4.83 brs;4.83 brs | H-12;H-14 |
| 14 | 36.60 | 2.78* | H-13a;H-14a;H-15;H-16;H-12 |
| 14a | 12.09 | 1.04 d(6.9) | H-15 |
| 15 | 75.34 | 5.12 dd(1.7,11) | H-13a;H-14a;H-16;H-16a |
| 16 | 47.62 | 3.04 dq(7,11) | H-15;H-16a |
| 16a | 13.73 | 1.15 d(7) | H-15;H-16 |
| 17 | 213.52 | | H-16;H-16a;H-18;H-15 |
| 18 | 51.94 | 2.62 brd(18) 2.86 dd(11,18) | H-16;H-20 |
| 19 | 66.16 | 4.00 brt(11) | H-18 |
| 20 | 37.70 | 0.97 ddd(12,12,12); 1.98* | H-18;H-22 |
| 21 | 73.98 | 3.46 tt(4,4,12,12) | H-22;H—OMe;H-20 |
| 22 | 44.18 | 1.08 t(12);1.99* | H-21;H-20 |
| 23 | 99.91 | | H-18;H-22;H-24;H-27 |
| 24 | 34.91 | 1.55*;2.28* | H-22 |
| 25 | 64.41 | 3.93 brm | H-26;H-27;H-24 |
| 26 | 39.11 | 1.57*;1.57* | H-28;H-24 |
| 27 | 61.22 | 5.00 ddd(4.3,10,10) | H-26;H-29 |
| 28 | 131.22 | 5.32 brt(10) | H-27;H-30 |
| 29 | 133.42 | 5.48 ddd(10,10,10) | H-27;H-30 |
| 30 | 28.07 | 2.00*;2.19* | H-28;H-29;H-31;H-32 |
| 31 | 27.04 | 1.23*;1.60* | H-29;H-33;H-30;H-32 |
| 32 | 32.82 | 1.30 m;1.42 m | H-33 |

-continued

| $^{13}C$ (100 MHz) | | XHCorr. (400 MHz) | HMBC(500 MHz, C to H) |
|---|---|---|---|
| 33 | 67.15 | 4.13 dt(3.4,3.4,8) | H-34a |
| 34 | 39.32 | 1.57 m | H-34a;H-36 |
| 34a | 11.55 | 0.81 d(7) | H-33;H-34 |
| 35 | 71.47 | 3.65 brs | H-34a;H-33;H-36 |
| 36 | 33.79 | 1.61*;1.89* | OH(C37);H-34 |
| 37 | 99.41 | | H-33;H-36;OH(C37),H-38 |
| 38 | 73.11 | 3.34 brs | H-36 |
| 39 | 81.30 | 3.72 brd(10) | H-40a;H-41 |
| 40 | 37.26 | 1.91* | H-40a;H-39;H-41 |
| 40a | 12.69 | 0.74 d(7) | H-40;H-41 |
| 41 | 80.60 | 4.75 dd(9,11) | H-40a;H-39;H-40; H-42;H-43 |
| 42 | 73.11 | 3.12 t(9) | H-40;H-41;H-43;H-40a |
| 43 | 78.72 | 3.39 brt(9) | H-39;H-41;H-42;H-44 |
| 44 | 40.24 | 2.08*;2.76 brd(13) | H-42;H-46;H-45a |
| 45 | 144.00 | | H-45a;H-43;H-44; H-46;H-47 |
| 45a | 116.61 | 4.86 brs;4.89 brs | H-44;H-46 |
| 46 | 43.93 | 2.33 brdd(7,14); 2.19* | H-44;H-45a |
| 47 | 70.13 | 4.36 ddd(6,7,11) | H-46;H-48 |
| 48 | 139.21 | 6.11 dd(6,15) | H-46;H-47 |
| 49 | 126.99 | 6.41 brd(15) | H-47;H-48;H-51 |
| 50 | 139.21 | | H-48;H-49;H-51 |
| 51 | 116.48 | 5.35 brs;5.45 brs | H-48;H-49 |
| OMe | 55.72 | 3.24 s | H-21 |
| OAc | 21.78 171.61 | 1.94 s | H—OAc($\delta$1.94);H-5 |
| OAc | 21.00 170.21 | 1.84 s | H—OAc($\delta$1.84);H-15 |
| OH (C25) | | 4.39 d(9.9) | |
| OH (C37) | | 4.73 d(2) | |
| OH (C9) | | 4.32 brs | |
| OH | | 3.83 brm | |

*Coupling constants for these signals were not measured due to overlapping.

* * * * *